United States Patent
Wu

(10) Patent No.: US 8,218,837 B2
(45) Date of Patent: Jul. 10, 2012

(54) MATERIAL COMPOSITION DETECTION FROM EFFECTIVE ATOMIC NUMBER COMPUTATION

(75) Inventor: Xiaoye Wu, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 978 days.

(21) Appl. No.: 12/134,890

(22) Filed: Jun. 6, 2008

(65) Prior Publication Data

US 2009/0304249 A1 Dec. 10, 2009

(51) Int. Cl.
*G06K 9/00* (2006.01)

(52) U.S. Cl. ........................... 382/128; 382/131

(58) Field of Classification Search .................. None
See application file for complete search history.

(56) References Cited

U.S. PATENT DOCUMENTS

| | | | |
|---|---|---|---|
| 6,487,274 B2 | 11/2002 | Bertsche | |
| 7,031,425 B2 | 4/2006 | Hsieh et al. | |
| 7,136,450 B2 | 11/2006 | Ying et al. | |
| 7,190,757 B2 | 3/2007 | Ying et al. | |
| 7,224,763 B2 | 5/2007 | Naidu et al. | |
| 7,298,812 B2 * | 11/2007 | Tkaczyk et al. | 378/5 |
| 2005/0271293 A1 | 12/2005 | Ying et al. | |
| 2006/0274066 A1 | 12/2006 | Ying et al. | |
| 2007/0014471 A1 | 1/2007 | Simanovsky et al. | |
| 2007/0014472 A1 | 1/2007 | Ying et al. | |
| 2007/0031036 A1 | 2/2007 | Naidu et al. | |
| 2009/0129539 A1 * | 5/2009 | Licato et al. | 378/5 |

OTHER PUBLICATIONS

M. Jansen and A. Bultheel, Multiple wavelet threshold estimation by generalized cross validation for images with correlated noise. IEEE Trans. Image Processing 8 7 (1999), pp. 947-953.*

* cited by examiner

*Primary Examiner* — Jason M Repko
*Assistant Examiner* — Thomas A James
(74) *Attorney, Agent, or Firm* — Marie-Claire Maple

(57) ABSTRACT

A technique is provided for computing an atomic number of materials forming an object imaged by a radiological modality. The method includes accessing a first monochromatic image and a second monochromatic image of the object, the first monochromatic image acquired at a first energy level and the second monochromatic image acquired at a second energy level. A ratio of the mass attenuation coefficients between the first monochromatic image and the second monochromatic image may be obtained. The atomic number for a material of the object may be computed based upon the ratio of mass attenuation coefficients.

16 Claims, 4 Drawing Sheets

MATERIAL COMPOSITION DETECTION FROM EFFECTIVE ATOMIC NUMBER COMPUTATION

BACKGROUND

The present invention relates generally to imaging systems, and more particularly to a method and system for determining a material composition of an imaged object by computing an effective atomic number.

Computed tomography (CT) systems generate two-dimensional (and in some cases, three-dimensional) images representative of an object or subject. In general, CT images may be presented in slices (or volumes) that are reconstructed from many projection images made at different angular positions around the object or subject. In many medical and industrial applications, it is often useful to determine the composition of materials imaged by these techniques. Such material identification may assist in determining what objects or structures are present in the subject. In medical imaging, for example, the material composition may be indicative of different tissue structures, such as soft tissue, bone, pathologies, and so forth. In other fields, such as package, luggage, and part inspection, other structures or objects of interest may be similarly identified by reference to the materials of which they are comprised.

Both CT systems and conventional X-ray imaging modalities provide representations of objects under examination in terms of attenuation coefficients, that is, the degree to which X-rays are attenuated by intervening structures between the source and detector. In typical CT imaging systems, the images generated usually provide information about linear attenuation coefficients of structures of the object. Linear attenuation coefficients are found to be useful when materials in the object are of the same density but may not be sufficient to provide density information of a material. Thus, linear attenuation coefficients are usually inadequate to characterize the material comprising an object.

There is a continuing need for improved methods and systems to compute material compositions in X-ray, CT and similar systems, and particularly that will permit determining or estimating effective atomic numbers for materials imaged.

BRIEF DESCRIPTION

Briefly, in accordance with one aspect of the technique, a method is provided for computing an atomic number of material scanned by a radiological modality. The method provides for accessing a first monochromatic image and a second monochromatic image of an object, where the first monochromatic image acquired at a first energy level and the second monochromatic image acquired at a second energy level. The method further includes obtaining a ratio of mass attenuation coefficients between the first monochromatic image and the second monochromatic image, and computing the atomic number for a material of the object based upon the ratio of mass attenuation coefficients. Systems and computer programs that afford such functionality may be provided by the present technique.

In accordance with another aspect of the present technique, an image analysis system is provided. The image analysis system includes an imaging source configured to produce an imaging beam and a detector configured to detect the imaging beam passing through object. The image analysis system further includes a processor configured to acquire a first monochromatic image and a second monochromatic image of the object, wherein the first monochromatic image is acquired at a first energy level and the second monochromatic image is acquired at a second energy level, and to compute a ratio of mass attenuation coefficients between pixels of the first monochromatic image and the second monochromatic image. The processor is also configured to compute an atomic number using the ratio of mass attenuation coefficients and analyze the atomic number to identify a material composition of the object. Here again, systems and computer programs affording such functionality may be provided by the present technique.

Various other features and advantages of the present technique will be made apparent from the following detailed description and drawings.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present technique is generally related to detection and characterization of materials present in an object. For example, such material detection may be employed to identify the presence of prohibited items (such as explosives, weapons, ammunition, radiological materials, chemical agents) in baggage, luggage, packages, or shipping containers. In certain embodiments, the detection and characterization of materials could be made through the computation of the atomic number (Z) of the material. In one embodiment, the atomic number may be an effective atomic number ($Z_{eff}$). As used herein, the term "effective atomic number" refers to the number of protons in the atoms nucleus, which distinguishes it from the atoms of other elements. It provides a measure of the electrostatic interaction between the negatively charged electrons and positively charged protons in the atom. As will be appreciated, the atomic number may be used to estimate the material composition of an object.

Figure 1:
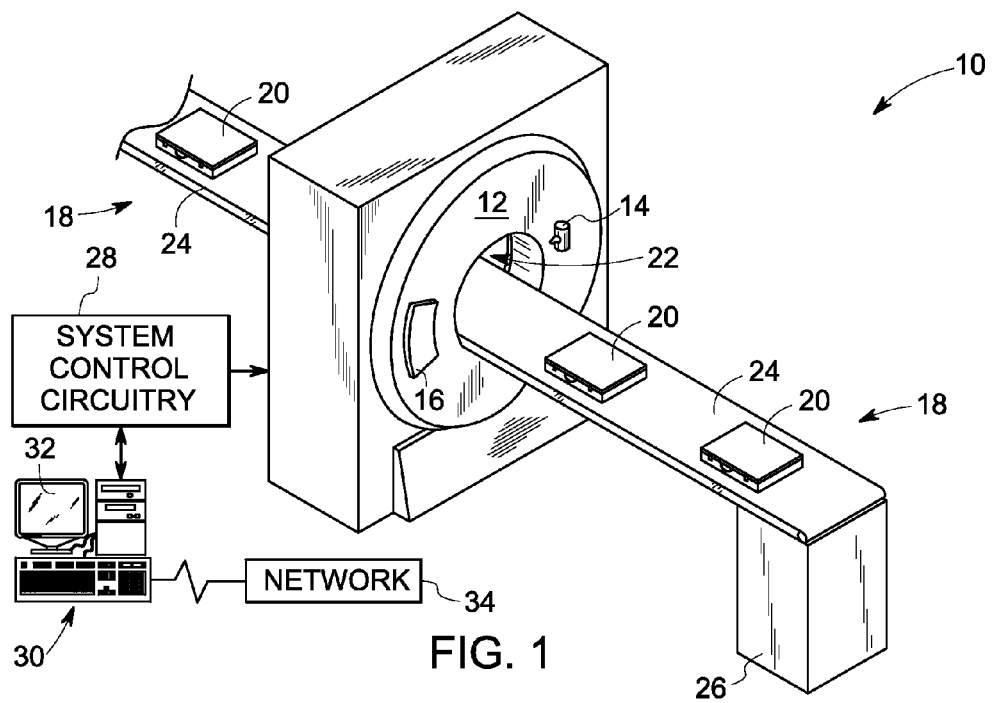
FIG. 1 is a perspective view of an exemplary CT system for use with a package inspection system.

Referring to FIG. 1, a computed tomography (CT) imaging system 10 is shown that is representative of a third generation CT scanner for scanning luggage, parcels, and packages. The CT imaging system 10 includes a gantry 12 with an imaging source 14 (i.e., X-ray source) that projects a beam of X-rays towards a detector 16 on the opposite side of the gantry 12. The detector module senses the projected X-rays that pass through an object. Each detector element produces an electrical signal that represents the intensity of an impinging X-ray beam and hence the attenuated beam as it passes through the object. It is contemplated that, in one embodiment, the detector 16 may be an energy integrating detector or a photon counting energy discriminating detector.

The CT imaging system 10 operates under the control of system control circuitry 28. The system control circuitry 28 may include a wide range of circuits such as radiation source control circuits, table motor controller, circuits for coordinating data acquisition in conjunction with baggage or table movement, circuits for controlling the position of the radiation source and/or the detector, and so forth. For example, in one embodiment, included system control circuitry may include circuits to control movement of the motorized conveyor system 18 during a scan when objects 20 are fed into the gantry opening 22. In such an embodiment, the motorized conveyor system 18 may include a conveyor belt 24 supported by structure 26 to automatically and continuously pass packages or baggage pieces through the gantry opening 22 to be scanned. As, the objects 20 fed through gantry opening 22 by conveyor belt 24 are scanned, imaging data may be acquired, and the conveyor belt 24 removes the packages from opening in a controlled and continuous manner.

Imaging data acquired during scan may be acquired by data acquisition circuitry for processing governed by a suitable control circuitry. Upon completion of processes, the image data may ultimately be forwarded to an operator interface 30 for viewing and analysis. The operator interface 30 may be employed for viewing preprocessed or reconstructed images based upon the image data collected. In the illustrated embodiment, the operator interface 30 is coupled to a monitor 32 for display of reconstructed images. Alternatively, the image data or reconstructed images can also be transferred to remote locations via a network 34, for example.

Figure 2:
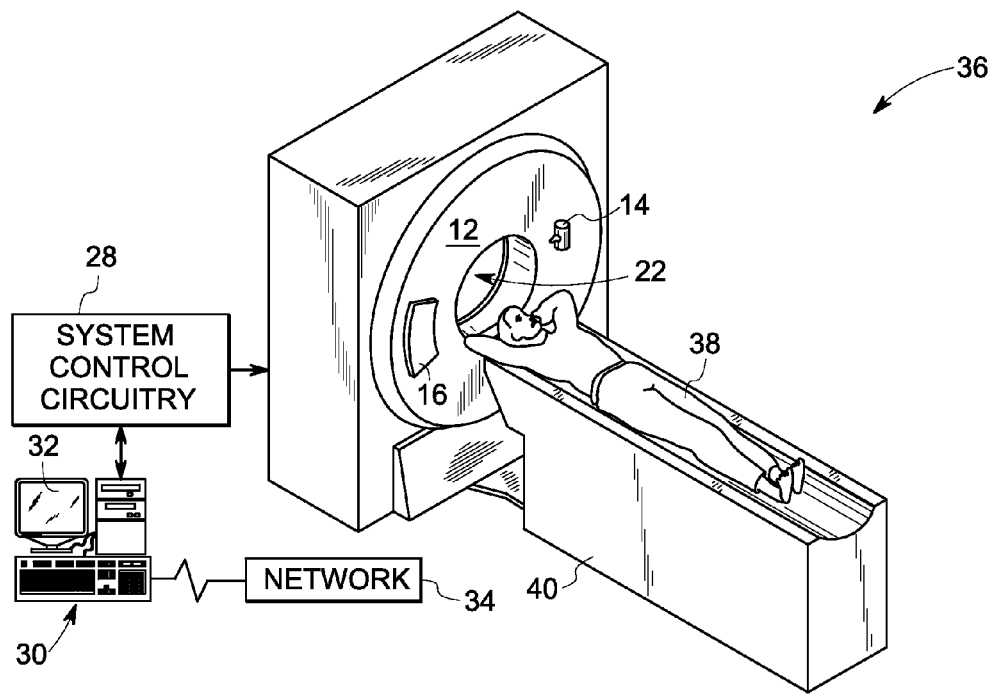
FIG. 2 is a perspective view of an exemplary CT imaging system as it might be used for medical diagnostic imaging.

As the present technique is also applicable with a CT scanner for medical diagnostic imaging, an exemplary CT imaging system useful for medical scanning 36 is illustrated in FIG. 2. However, as will be appreciated by those skilled in the art, the medical imaging system 36 of FIG. 2 also includes the components associated with FIG. 1. However, the patient 38 is translated into the gantry opening 22 in either continuous or incremental manner by table 40. Various operational components and associated control circuitry of the imaging systems 10 and 36 are elaborated upon in FIG. 3 below.

Figure 3:
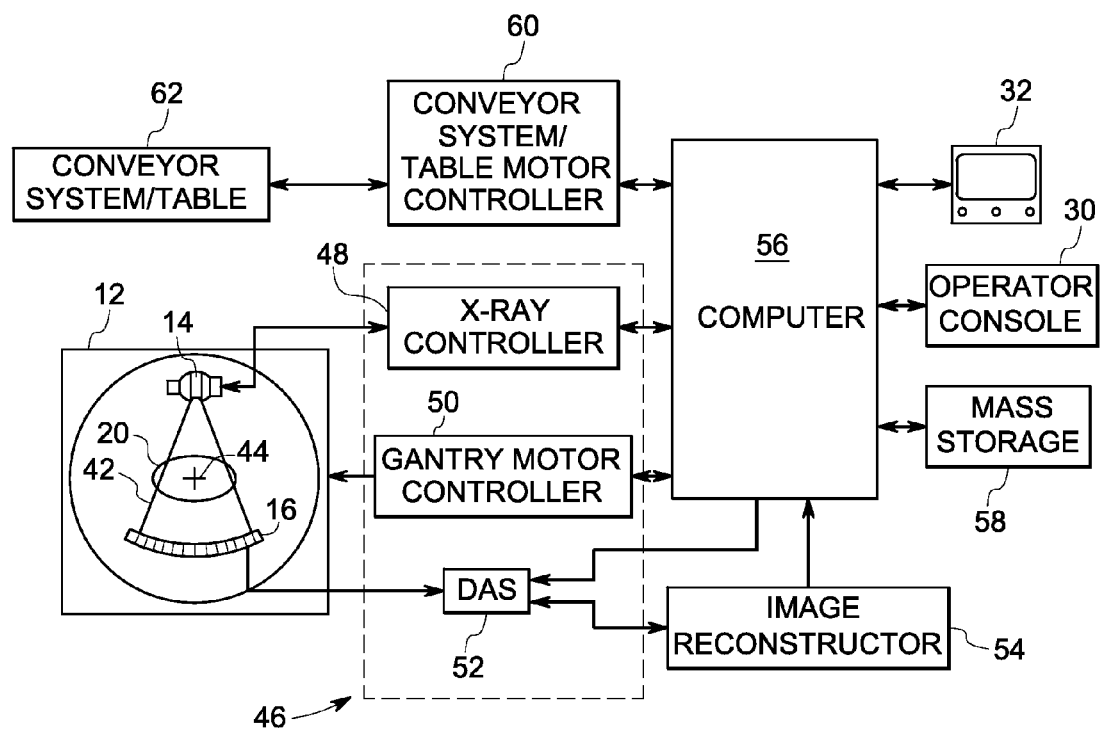
FIG. 3 is a schematic diagram of certain of the operational components of the system illustrated in FIG. 1 and FIG. 2.

The operational components of the gantry 12 represented in FIG. 3 include an X-ray source 14 configured to emit beam of X-rays 42. The gantry 12 also includes a detector 16 for detecting the X-rays. In one embodiment, the gantry 12, along with the X-ray source and detector, have components mounted thereon to rotate about the center of rotation 44. The rotation of gantry 12 and the operation of X-ray source 14 are governed by a control mechanism 46 of the CT imaging system, such as systems 10 and 36. Control mechanism 46 includes an X-ray controller 48 that provides power and timing signals to the X-ray source 14 and a gantry motor controller 50 that controls the rotational speed and position of gantry 12. An image reconstructor 54 receives sampled and digitized image data from data acquisition system (DAS) 52 and performs high speed reconstruction. The reconstructed image is applied as an input to a computer 56, which stores the image in a mass storage device 58.

Computer 56 also receives commands and scanning parameters from an operator via console 30 or operator interface that has a keyboard. An associated display 32 allows the operator to observe the reconstructed image and other data from computer 56. The operator supplied commands and parameters are used by computer 56 to provide control signals and information to DAS 52, X-ray controller 48 and gantry motor controller 50. In addition, computer 56 may operate a table motor controller or conveyor system motor controller 60, which controls a motorized table or conveyor system 62 respectively to position an object 20 (or patient 38 in medical contexts), through a gantry opening 22. As a result, postal inspectors, baggage handlers, and other security personnel may non-invasively inspect the contents of the packages for explosives knives, guns, contraband, etc.

Figure 4:
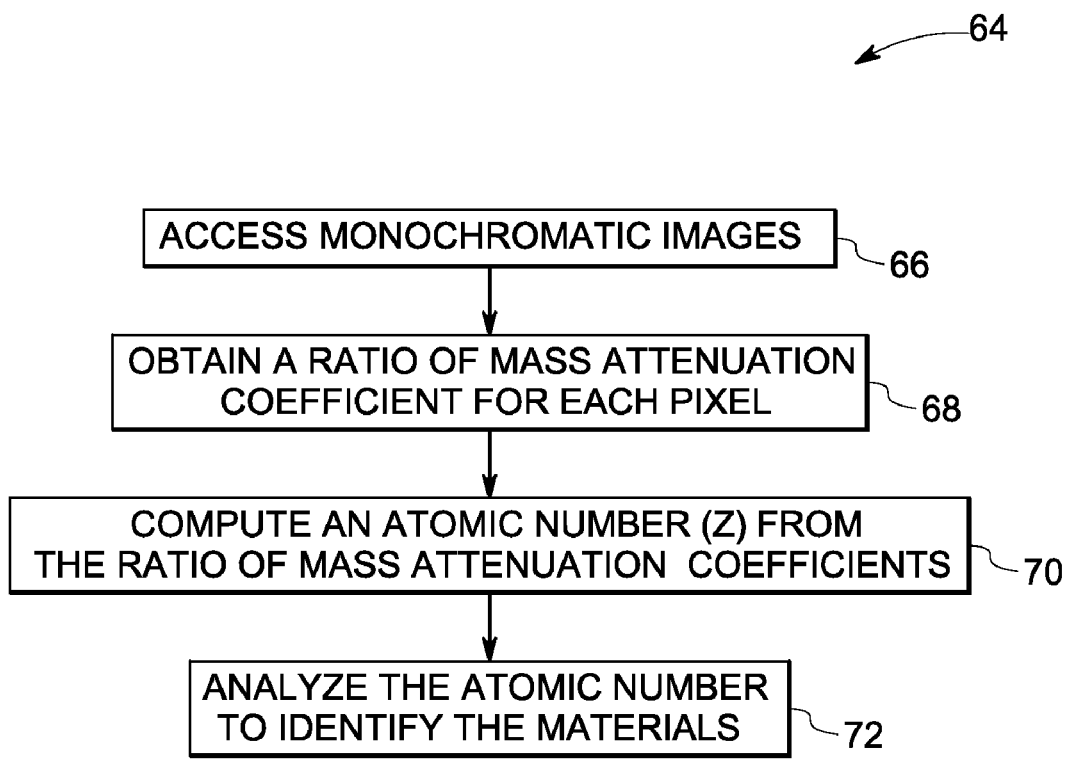
FIG. 4 is a flow chart setting forth exemplary steps of computing effective atomic number from monochromatic images generated by the imaging through CT imaging system.

In the illustrated embodiment of FIG. 4, a flow chart 64 illustrates a method of computing an atomic number of a material examined by a radiological modality. The method includes accessing (in block 66) a first monochromatic image and a second monochromatic image of an object, where the monochromatic images are obtained at different energy levels. Moreover, the first and second monochromatic images at two different energies may be obtained using a monochromatic X-ray source or a polychromatic X-ray source. For example, in one embodiment, the first and second monochromatic images are acquired or obtained using a polychromatic source by computing the equivalent monochromatic representation from the dual energy projection data. A number of techniques may be used to acquire the dual energy scan data, produced by an imaging source of at least two different energy levels. For example, the X-ray tube may be alternatively biased between a high Kilovoltage Peak (kVp) and a low kVp, or a dynamic filter may be controlled such that the X-ray beam attenuated by the object to be imaged is cycled between high energy and low energy. It is also contemplated that a combination of X-ray tube and X-ray filter control may also be used to acquire dual energy data at different energy levels. Other methods such as dual energy CT systems, X-ray systems, and other multiple energy techniques are also contemplated for use in the present technique.

An exemplary algorithm for deriving such monochromatic images uses basis material decomposition (BMD) techniques, although it is envisioned that other suitable decomposition techniques may also be used. In one embodiment, the dual energy projection data are reconstructed to obtain material density images of basis materials, and on further computation yields the derived monochromatic images. The derived monochromatic images include the first and second monochromatic images generated at different energies that are representative of the sum of the basis material density images weighted by basis material mass attenuation coefficients.

In one embodiment, the first monochromatic image is acquired at a high energy level, and a second monochromatic image is acquired at a low energy level via a processor based image analysis system. The choice of first and second energies in the energy region, when there are no K-edges, may not affect the final computational result of atomic number value, provided there is sufficient separation between the two energies. The first monochromatic image at the first energy level ($E_1$) and second monochromatic image at a second energy level ($E_2$) may be represented as, $$\text{Mono\_}E1\ (i,j) = u1(E1)Im1(i,j) + u2(E1)Im2(i,j) \quad \text{(Eq. 1)}$$

$$\text{Mono\_}E2\ (i,j) = u1(E2)Im1(i,j) + u2(E2)Im2(i,j) \quad \text{(Eq. 2)}$$

where, $u_1(E_1)$ and $u_2(E_2)$ are the mass attenuation coefficients at energies $E_1$ and $E_2$ for basis material 1 and 2 respectively, and Im1(i, j) and Im2(i, j) are the density images of the two basis materials. In the illustrated embodiment, it should be appreciated that any suitable high or low energy levels may be used to derive monochromatic images. Further, the mass attenuation coefficients in Equation 1 and Equation 2 may represent any suitable type of basis material, depending on the scanning context. For example, in a medical context, the mass attenuation coefficients may correspond to soft tissue or bone while in a security context the mass coefficients may instead correspond to steel, an explosive, or other materials having different attenuation characteristics. In addition, the technique is contemplated for use with monochromatic images of more than two basis materials as well.

As discussed above, the use of known effective energies gives an estimate of expected attenuation for different materials, and hence the information on material composition or tissue composition can be extracted. At block 68, a ratio of the mass attenuation coefficients is obtained for each pixel of interest between a first and a second monochromatic image. Each pixel corresponds to a picture element of a derived monochromatic image, and thus each pixel represents the attenuation coefficient of the material being imaged. In one embodiment the ratio of mass attenuation coefficients is obtained from the ratio of linear attenuation coefficients. The linear attenuation coefficient is obtained for a pixel in the first monochromatic image and for a corresponding pixel in the second monochromatic image i.e., on a pixel-by-pixel basis. As will be appreciated, the linear attenuation coefficient is dependent on the density of the material and is a function of energy of the radiation. Hence, when the ratio of linear attenuation coefficients is obtained the density parameter of the two linear attenuation coefficients are nullified by each other. Therefore, the ratio of linear attenuation coefficients at given energy levels is the same as the ratio of mass attenuation coefficients at those energy levels. Specifically, the attenuation ratio pairs for high and low energies using known elementary materials are obtained using Equation 3 as, $$r = uZ(E1)/uZ(E2) \quad \text{(Eq. 3)}$$

where $uZ(E_1)$ and $uZ(E_2)$ are the mass attenuation coefficients of an elementary material with atomic number Z at energy $E_1$ and $E_2$.

At block 70, an atomic number is computed for one or more materials from the ratio of mass attenuation coefficients in the depicted embodiment. At block 72, the atomic number is analyzed with known material compositions to identify the materials in the object. Optionally, the flowchart 64 may include a step of generating an atomic number image (i.e., a Z-image) for viewing and diagnosis. In the embodiments illustrated, flowchart and/or automated routines for performing the techniques and steps described herein may be implemented by the imaging systems 10 and 36 of FIGS. 1 and 2 respectively or by any other suitably configured processor based image analysis system, either by hardware, software, or combinations of hardware and software. For example, suitable code stored in memory or on hard disk may be accessed and executed by the computer 56, or application specific integrated circuits (ASICs) may be configured to perform some or all of the techniques described herein.

Figure 5:
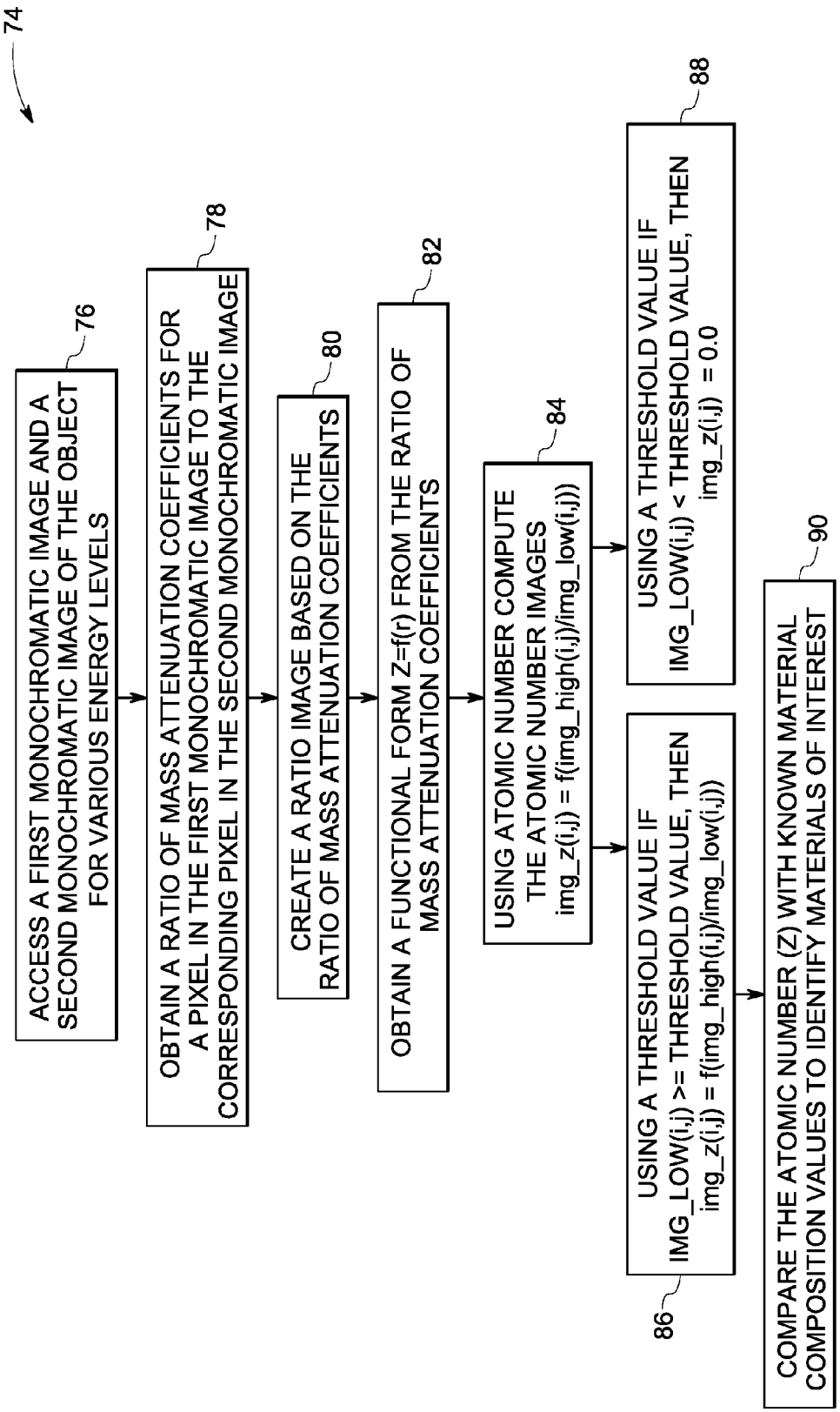
FIG. 5 is a flow chart illustrating an exemplary process for computing effective atomic number in detail, based on a threshold value.

By means of further example, the atomic number computation as represented by blocks 70 and 72 of FIG. 4 may be further elaborated as shown in FIG. 5. In the illustrated embodiment of FIG. 5, the flow chart 74 includes the blocks 76 and 78 that generally correspond to the blocks 66 and 68, respectively, of the flow chart 64 of FIG. 4. As explained in greater detail with regard to blocks 66 and 68 of FIG. 4, at block 76 a first monochromatic image and a second monochromatic image are accessed that are at different energy levels. At block 78, a ratio of mass attenuation coefficients is obtained on a pixel-by-pixel basis between respective pixels in the first and second monochromatic images.

As will be appreciated, based on the ratio of mass attenuation coefficients or the attenuation ratio pairs between two energy levels in block 78, a ratio image may be generated at block 80. Further, the ratio image could be a composite of the first monochromatic image and the second monochromatic image. In one embodiment, the pixels of the ratio image are transformed to get an effective Z-image. Hence, a relationship may be established through the functional form to determine a transfer function from the ratio of mass attenuation coefficients. In other words, the transfer function is determined by computing the ratio of the mass attenuation coefficients of two or more known elements at the first and second energy levels. For example, in one embodiment, using the ratio of mass attenuation coefficients of elements (for example, with atomic numbers from 5 to 20) the data points are fitted with a fifth order polynomial. In such an embodiment, use of a higher order polynomial may allow suitable fitting of the data points. Moreover, the selection of elements in obtaining the transfer function should cover the range of possible Z values that the CT system is designed to image or the range of interest.

The data points fitted from these measures yield (block 82) a transfer function, or for example a functional form of $Z=f(r)$, with r as expressed in Equation 3. Furthermore, the transfer function may be determined based on a predetermined threshold value. In such an embodiment, the predetermined threshold value may correspond to the image or noise value, as discussed below. Thus the atomic number may be computed for a material of the object from the ratio of attenuation coefficients by applying a transfer function.

In general, the atomic number is compared with a look up table by means of computer-aided techniques. In one embodiment, the effective atomic number image may be generated in block 84 by transforming a ratio image based on a threshold value. Hence, in one embodiment, in order to compute a Z-image at block 86 and 88, certain threshold values may be set such that, $$Im\_Z(i,j) = f(Im\_E1(i,j)/Im\_E2(i,j)), \quad \text{if} \quad Im\_E2(i,j) \geq \text{threshold value}$$

and $$Im\_Z(i,j) = 0.0, \text{ if } Im\_E2(i,j) < \text{threshold value}$$

where the threshold value is set to some multiple of the image noise in $Im\_E_2(i, j)$ to avoid extracting effective Z images in the null material region in the images. In one embodiment, such as in medical imaging, any material with a linear attenuation value less than 0.05/cm, and with an energy range of about 40 to 140 keV may be of little interest for diagnosis, and hence the threshold measure can be set to this value. In certain automated embodiments, a computer is programmed to perform such techniques, or a computer readable storage medium is provided that encodes a set of instructions that when executed by the computer generates effective Z images. In such an implementation, the atomic number may be analyzed (block 86) by comparing the atomic number computed with a known material composition value to identify the material in block 90.

Alternatively, in another embodiment, an atomic number image may be generated when the first and second monochromatic images represented in Equations 1 and 2 are transformed based on a threshold value. As the pixels of the monochromatic images represent the attenuation coefficients at a location in the object, the ratio of attenuation coefficients at the same pixel can be converted into Z value using the transfer function. As mentioned, use of a threshold value can eliminate image regions where there is no presence of material, and hence atomic map information can be useful to compute the effective Z-image.

Effective Z images may be used to identify objects in both baggage inspection systems (i.e., non medical) and medical diagnosis. For example, during medical diagnosis, the present technique provides atomic number data, and an estimation of material composition of elements or materials can be provided, through which the presence of any abnormalities can be determined.

As will be appreciated by those skilled in the art, the techniques described in various embodiments discussed above provide effective Z images, and with fast computing speed, thereby improving efficiency and accuracy. The accurate computation of Z number may also improve the inspection of luggages and diagnostic capability of radiologists and/or physicians. Further, the monochromatic images for computing effective Z may be selected to have reduced noise as compared to the density images. Hence, the computation of effective Z from monochromatic images provides a robust method of Z capture. Also, the monochromatic images employed can be obtained for various energy levels independent of machine characteristics and data acquisition methods.

Though the present embodiments provide examples with respect to security inspection system, the present techniques may be employed in medical imaging contexts as well. Moreover, although the embodiments described herein provide examples with respect to monochromatic images acquired via a dual energy computed tomography system, the technique may be applied or extended to imaging modalities employing multiple energy sources and so forth.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of computing an atomic number of a material examined by a radiological modality, the method comprising:
   accessing a first monochromatic image and a second monochromatic image of an object, the first monochromatic image acquired at a first energy level and the second monochromatic image acquired at a second energy level;
   obtaining a ratio of mass attenuation coefficients between the first monochromatic image and the second monochromatic image; and
   generating a ratio image based on the ratio of mass attenuation coefficients, wherein the ratio image is a composite of the first monochromatic image and the second monochromatic image;
   determining a transfer function by computing the ratio of mass attenuation coefficients of two or more elements at the first and second energy levels based on a predetermined threshold value;
   applying the transfer function to the ratio image for computing the atomic number for a material of the object based upon the ratio of mass attenuation coefficients.

2. The method of claim 1, comprising computing the first monochromatic image and the second monochromatic image via a material decomposition technique.

3. The method of claim 1, wherein the first monochromatic image and the second monochromatic image are obtained from material density images.

4. The method of claim 1, wherein the ratio of mass attenuation coefficients is obtained on a pixel-by-pixel basis based on the first monochromatic image and the second monochromatic image.

5. The method of claim 1, wherein the predetermined threshold value corresponds to an image noise value or a minimum linear attenuation value of the application.

6. The method of claim 1, further comprising analyzing the atomic number to identify material composition of the object.

7. The method of claim 6, wherein analyzing comprises comparing the atomic number with a look-up table.

8. The method of claim 1, further comprising generating an atomic number image by transforming a ratio image based on a threshold value.

9. The method of claim 1, further comprising generating an atomic number image by transforming the first monochromatic image and the second monochromatic image based on a threshold value.

10. An image analysis system comprising:
    an imaging source configured to produce an imaging beam;
    a detector configured to detect the imaging beam passing through an object; and
    a processor configured to:
    acquire a first monochromatic image and a second monochromatic image of the object, wherein the first monochromatic image is acquired at a first energy level and the second monochromatic image is acquired at a second energy level;
    compute a ratio of mass attenuation coefficients between one or more pixels of the first monochromatic image and the second monochromatic image;
    generate a ratio image based on the ratio of mass attenuation coefficients, wherein the ratio image is a composite of the first monochromatic image and the second monochromatic image;
    determine a transfer function by computing the ratio of mass attenuation coefficients of two or more elements at the first and second energy levels based on a predetermined threshold value;
    apply the transfer function to the ratio image for computing an atomic number based upon the ratio of mass attenuation coefficients; and
    analyze the atomic number to identify a material composition of the object.

11. The image analysis system of claim 10, wherein the imaging source is configured to emit X-rays at two different energy levels.

12. The image analysis system of claim 10, wherein the processor is further configured to obtain projection data of the object for at least two different spectra, decompose the projection data to obtain material density images, and derive the monochromatic images from the material density images.

13. The image analysis system of claim 10, wherein the processor is configured to obtain the ratio of mass attenuation coefficients on a pixel-by-pixel basis based on the first monochromatic image and the second monochromatic image.

14. A non-transitory computer readable storage medium that stores instructions executable by one or more processors to perform a method of computing an atomic number of a material examined by a radiological modality, comprising
    accessing a first monochromatic image and a second monochromatic image of object, wherein the first monochromatic image is acquired at a first energy level and the second monochromatic image is acquired at a second energy level;
    obtaining a ratio of mass attenuation coefficients between the monochromatic images;
    generating a ratio image based on the ratio of mass attenuation coefficients, wherein the ratio image is a composite of the first monochromatic image and the second monochromatic image;
    determining a transfer function by computing the ratio of mass attenuation coefficients of two or more elements at the first and second energy levels based on a predetermined threshold value; and
    applying the transfer function to the ratio image to compute an atomic number for a material of the object based upon the ratio of mass attenuation coefficients.

15. The non-transitory computer readable storage medium of claim 14, comprising instructions to obtain the ratio of mass attenuation coefficients on a pixel-by-pixel basis based on the first monochromatic image and the second monochromatic image.

16. The non-transitory computer readable storage medium of claim 14, further comprising instructions to analyze the atomic number to identify material composition of the object.

* * * * *